(12) United States Patent
Wang et al.

(10) Patent No.: US 11,608,979 B2
(45) Date of Patent: Mar. 21, 2023

(54) LED TUBE APPARATUS

(71) Applicant: XIAMEN LEEDARSON LIGHTING CO. LTD, Fujian (CN)

(72) Inventors: Linhua Wang, Fujian (CN); Liangliang Cao, Fujian (CN)

(73) Assignee: XIAMEN LEEDARSON LIGHTING CO. LTD, Fujian (CN)

( * ) Notice: Subject to any disclaimer, the term of this patent is extended or adjusted under 35 U.S.C. 154(b) by 0 days.

(21) Appl. No.: 16/916,555

(22) Filed: Jun. 30, 2020

(65) Prior Publication Data

US 2021/0404646 A1 Dec. 30, 2021

(51) Int. Cl.
| | |
|---|---|
| *F21V 33/00* | (2006.01) |
| *F21V 23/00* | (2015.01) |
| *F21V 23/04* | (2006.01) |
| *F21V 29/67* | (2015.01) |
| *A61L 2/24* | (2006.01) |
| *A61L 2/10* | (2006.01) |
| *A61L 9/20* | (2006.01) |
| *A01M 1/04* | (2006.01) |
| *A01M 1/22* | (2006.01) |
| *A01M 1/10* | (2006.01) |

(Continued)

(52) U.S. Cl.
CPC ........... *F21V 33/0064* (2013.01); *A01M 1/04* (2013.01); *A01M 1/106* (2013.01); *A01M 1/223* (2013.01); *A61L 2/10* (2013.01); *A61L 2/24* (2013.01); *A61L 9/20* (2013.01); *F21K 9/27* (2016.08); *F21V 23/003* (2013.01); *F21V 23/0435* (2013.01); *F21V 23/0471* (2013.01); *F21V 29/677* (2015.01); *A61L 2202/11* (2013.01); *A61L 2202/14* (2013.01); *A61L 2209/111* (2013.01); *A61L 2209/12* (2013.01); *A61L 2209/16* (2013.01); *F21Y 2113/10* (2016.08); *F21Y 2115/10* (2016.08)

(58) Field of Classification Search
CPC .......... A61L 2/10; A61L 9/20; A61L 2202/11; A61L 2209/12; F21V 19/008; F21V 7/005; F21Y 2107/40; F21Y 2107/90; A01M 1/04
See application file for complete search history.

(56) References Cited

U.S. PATENT DOCUMENTS 1,185,602 A * 5/1916 Leal-Quiroz ........... C10B 11/00
202/130
4,248,005 A * 2/1981 Hedstrom ............... A01M 1/04
43/112

(Continued)

*Primary Examiner* — Colin J Cattanach
(74) *Attorney, Agent, or Firm* — Chun-Ming Shih; Lanway IPR Services

(57) ABSTRACT

A light tube apparatus includes a tubular housing, a first light source, a second light source, a driver and a controller. The tubular housing having a first light passing window and a second light passing window. The first light source is for emitting a white light from the first light passing window in an illuminating mode. The second light source is for emitting an ultraviolet light from the second light passing window in a sanitizing mode. The driver is for converting an external power source to a first driving current to the first light source and a second driving current to the second light source. The controller is for determining when to enter the sanitizing mode or the illuminating mode based on a stored criterion.

13 Claims, 9 Drawing Sheets

(51) Int. Cl.
   *F21K 9/27*      (2016.01)
   *F21Y 113/10*    (2016.01)
   *F21Y 115/10*    (2016.01)

(56)           References Cited

U.S. PATENT DOCUMENTS

| | | | | |
|---|---|---|---|---|
| 6,264,888 | B1* | 7/2001 | Palestro | A61L 9/20 |
| | | | | 422/24 |
| 6,494,940 | B1* | 12/2002 | Hak | A61L 9/16 |
| | | | | 55/471 |
| 8,350,228 | B2 | 1/2013 | Welker | A61L 9/20 |
| | | | | 250/455.11 |
| 8,651,704 | B1* | 2/2014 | Gordin | F21V 33/0092 |
| | | | | 362/294 |
| 8,791,441 | B1* | 7/2014 | Lichtblau | A61L 9/20 |
| | | | | 250/504 R |
| 9,370,600 | B1* | 6/2016 | DuPuis | A61L 9/20 |
| 9,867,894 | B2* | 1/2018 | Stibich | A61L 2/20 |
| 10,166,309 | B2* | 1/2019 | Liao | H05B 45/10 |
| 10,363,327 | B2* | 7/2019 | Liao | C02F 1/008 |
| 10,556,025 | B2* | 2/2020 | Ufkes | A61L 2/28 |
| 10,792,381 | B2* | 10/2020 | Poulsen | F21S 8/063 |
| 2005/0186108 | A1* | 8/2005 | Fields | A61L 9/015 |
| | | | | 422/4 |
| 2007/0053188 | A1* | 3/2007 | New | B64D 13/00 |
| | | | | 362/276 |
| 2009/0004046 | A1* | 1/2009 | McEllen | A61L 9/20 |
| | | | | 422/2 |
| 2009/0191100 | A1* | 7/2009 | Deal | A61L 2/10 |
| | | | | 422/105 |
| 2010/0044319 | A1* | 2/2010 | Engel | H05B 41/39 |
| | | | | 210/746 |
| 2010/0196214 | A1* | 8/2010 | Graff | F24F 13/078 |
| | | | | 422/121 |
| 2011/0058372 | A1* | 3/2011 | Lerman | H05K 1/0204 |
| | | | | 362/235 |
| 2011/0180818 | A1* | 7/2011 | Lerman | H01L 25/0753 |
| | | | | 257/88 |
| 2012/0126134 | A1* | 5/2012 | Deal | A61L 2/24 |
| | | | | 250/372 |
| 2012/0199005 | A1* | 8/2012 | Koji | F21V 33/0088 |
| | | | | 96/224 |
| 2013/0291735 | A1* | 11/2013 | Livchak | A61L 9/20 |
| | | | | 96/224 |
| 2014/0334137 | A1* | 11/2014 | Hasenoehrl | F21V 23/001 |
| | | | | 362/147 |
| 2015/0062893 | A1* | 3/2015 | Lynn | A61L 2/10 |
| | | | | 362/231 |
| 2015/0086420 | A1* | 3/2015 | Trapani | A61L 9/015 |
| | | | | 422/24 |
| 2015/0165079 | A1* | 6/2015 | Shur | F25D 17/042 |
| | | | | 250/455.11 |
| 2016/0317690 | A1* | 11/2016 | Dayton | A61L 9/00 |
| 2017/0006847 | A1* | 1/2017 | McGowan | A01M 1/145 |
| 2017/0049915 | A1* | 2/2017 | Brais | A61L 2/10 |
| 2017/0188563 | A1* | 7/2017 | Lee | F21V 23/04 |
| 2017/0307242 | A1* | 10/2017 | Handsaker | F24F 11/30 |
| 2017/0321877 | A1* | 11/2017 | Polidoro | F24F 13/28 |
| 2018/0185527 | A1* | 7/2018 | Lalicki | A61L 2/0052 |
| 2018/0185533 | A1* | 7/2018 | Lalicki | A61L 2/24 |
| 2018/0347574 | A1* | 12/2018 | Niemiec | F21S 10/06 |
| 2019/0072288 | A1* | 3/2019 | Niemiec | F21V 33/0096 |
| 2019/0113219 | A1* | 4/2019 | Niemiec | F21V 29/677 |
| 2019/0167826 | A1* | 6/2019 | Winslow | F21V 15/015 |
| 2019/0178456 | A1* | 6/2019 | Niiyama | F21V 9/08 |
| 2019/0249847 | A1* | 8/2019 | Hallack | F21V 23/0442 |
| 2019/0254143 | A1* | 8/2019 | Hallack | F21V 21/28 |
| 2019/0320515 | A1* | 10/2019 | Sadwick | H05B 45/00 |
| 2019/0338895 | A1* | 11/2019 | Jeswani | F21V 23/04 |
| 2019/0358584 | A1* | 11/2019 | Pen | A61L 9/122 |
| 2019/0360686 | A1* | 11/2019 | Pendo | F21V 33/0096 |
| 2020/0009286 | A1* | 1/2020 | Zarcone | F21V 23/003 |
| 2020/0053856 | A1* | 2/2020 | Barber | H05B 45/12 |
| 2020/0179544 | A1* | 6/2020 | Ufkes | H05B 45/20 |
| 2020/0188542 | A1* | 6/2020 | Lei | A61L 2/08 |
| 2020/0230271 | A1* | 7/2020 | Choi | F21V 1/20 |
| 2020/0289698 | A1* | 9/2020 | Polidoro | F21V 21/04 |
| 2021/0077643 | A1* | 3/2021 | Dombrowsky | A47L 9/2847 |
| 2021/0348783 | A1* | 11/2021 | Adkins | F24F 8/22 |

\* cited by examiner

LED TUBE APPARATUS

FIELD

The present invention is related to a lighting fixture and more particularly related to a LED light tube.

BACKGROUND

Lighting or illumination is the deliberate use of light to achieve a practical or aesthetic effect. Lighting includes the use of both artificial light sources like lamps and light fixtures, as well as natural illumination by capturing daylight. Daylighting (using windows, skylights, or light shelves) is sometimes used as the main source of light during daytime in buildings. This can save energy in place of using artificial lighting, which represents a major component of energy consumption in buildings. Proper lighting can enhance task performance, improve the appearance of an area, or have positive psychological effects on occupants.

Indoor lighting is usually accomplished using light fixtures and is a key part of interior design. Lighting can also be an intrinsic component of landscape projects.

A light-emitting diode (LED) is a semiconductor light source that emits light when current flows through it. Electrons in the semiconductor recombine with electron holes, releasing energy in the form of photons. This effect is called electroluminescence. The color of the light (corresponding to the energy of the photons) is determined by the energy required for electrons to cross the band gap of the semiconductor. White light is obtained by using multiple semiconductors or a layer of light-emitting phosphor on the semiconductor device.

Appearing as practical electronic components in 1962, the earliest LEDs emitted low-intensity infrared light. Infrared LEDs are used in remote-control circuits, such as those used with a wide variety of consumer electronics. The first visible-light LEDs were of low intensity and limited to red. Modern LEDs are available across the visible, ultraviolet, and infrared wavelengths, with high light output.

Early LEDs were often used as indicator lamps, replacing small incandescent bulbs, and in seven-segment displays. Recent developments have produced white-light LEDs suitable for room lighting. LEDs have led to new displays and sensors, while their high switching rates are useful in advanced communications technology.

LEDs have many advantages over incandescent light sources, including lower energy consumption, longer lifetime, improved physical robustness, smaller size, and faster switching. Light-emitting diodes are used in applications as diverse as aviation lighting, automotive headlamps, advertising, general lighting, traffic signals, camera flashes, lighted wallpaper and medical devices.

Unlike a laser, the color of light emitted from an LED is neither coherent nor monochromatic, but the spectrum is narrow with respect to human vision, and functionally monochromatic.

The energy efficiency of electric lighting has increased radically since the first demonstration of arc lamps and the incandescent light bulb of the 19th century. Modern electric light sources come in a profusion of types and sizes adapted to many applications. Most modern electric lighting is powered by centrally generated electric power, but lighting may also be powered by mobile or standby electric generators or battery systems. Battery-powered light is often reserved for when and where stationary lights fail, often in the form of flashlights, electric lanterns, and in vehicles.

Although lighting devices are widely used, there are still lots of opportunity and benefit to improve the lighting devices to provide more convenient, low cost, reliable and beautiful lighting devices for enhancing human life.

SUMMARY

A light tube apparatus includes a tubular housing, a first light source, a second light source, a driver and a controller. The tubular housing has a first light passing window and a second light passing window. The first light source is for emitting a white light from the first light passing window in an illuminating mode, and the second light source is for emitting an ultraviolet light from the second light passing window in a sanitizing mode. The driver is for converting an external power source to a first driving current to the first light source and a second driving current to the second light source. The controller is for determining when to enter the sanitizing mode or the illuminating mode based on a stored criterion.

In some embodiments, the light tube apparatus includes the tubular housing. There are two end caps fixed on two ends of the tubular housing. There are pins fixed the cap end for connecting to a light tube socket to receive electricity from a power source.

In some embodiments, the light tube apparatus also has a first window and a second window disposed on surface of the tubular housing.

In some embodiments, the light tube apparatus has a first light source, a second light source, a driver and a controller. The driver converts an external power source like a 110V alternating current power source to a direct current.

In some embodiments, the controller contains one or multiple circuits working the driver to control the first light source and the second light source. The first light source emits a white light or other light to provide illumination function. The second light source emits an ultraviolet light to provide a sanitizing function. The controller determines when to enter a sanitizing mode in which the second light source is operated to clean air or surface of objects. In addition to using ultraviolet light for sanitization, the second light source may be used to generate ozone which also has sanitization function. Usually, people may not want to be exposed to ultraviolet light environment. Therefore, the controller is provided with a criterion to automatically or selectively determine when and whether to enter or pause the sanitizing mode.

There are various ways to arrange the first window and the second window. In some embodiments, the first light source and corresponding first window are located at a central portion of the light tube apparatus. The second light source and the second window are located at two ends of the light tube.

In some embodiments, the light tube apparatus also includes a motion sensor. The controller pauses the sanitizing mode when a user is detected by the motion sensor.

In some embodiments, there is a motion sensor installed to the light tube apparatus for detecting whether there is person nearby. For example, the motion sensor may be made of an infrared sensor or a radar sensor. The infrared sensor uses infrared detection of people. The radar sensor uses microwave to detect whether there are people moving near or staying below the light tube.

As mentioned above, the controller using a criterion may be one or multiple rules coded in program or logic circuits in the controller, to determine when to enter or to pause the sanitizing mode. Designers may set the criterion as that when a person nearby is detected by the motion sensor, the controller stops the sanitizing mode immediately until the detected person leaves the detected area.

In some embodiments, the criterion may be set that the controller starts the sanitizing mode when no one is detected in the detected area. In other words, when no one is in the place, like a living room or an office, the second light source is turned on to emit ultraviolet light to perform sanitization in the detected area.

In some embodiments, the controller automatically determines whether to enter the sanitizing mode when no one is detected by the motion sensor.

In some embodiments, the criterion may be more complicated with multiple rules. For example, the controller also refers to a timer to determine whether to enter the sanitizing mode. For example, when the controller finds that it is later than 23:00, the sanitizing mode is turned on until 04:00.

In some embodiments, the light tube apparatus further includes a rotation ring for rotating the second window so that the ultraviolet light automatically scans a predetermined area.

In some embodiments, the light tube apparatus has a rotation ring for rotating the second window and the second light source, if necessary, to change an emitted zone.

In some embodiments, a lens that is used for changing an area size may also be used for adjusting the sanitizing area.

In some embodiments, the tubular housing has a manual switch electrically connected to the controller for enabling or disabling the sanitizing mode.

In some embodiments, the controller may also be connected to a switch. The switch may be a manual switch like a jumper disposed on a surface of the light tube apparatus. The switch may also be a voice activated switch or a touch activated switch to turn on, to turn off, to disable or to enable the sanitizing function.

In some embodiments, the switch may be used for changing an operating mode of the light tube. For example, during summer vacation, the light tube may be set by operating the switch to enter the sanitizing mode every day between 23:00 to 05:00 automatically while the first light source module is not turned on.

In some embodiments, the tubular housing has an infrared receiver electrically connected to the controller for turning on or turning off the sanitizing mode.

In some embodiments, the light tube apparatus may also have a wireless module. For example, the wireless module may be an infrared receiver for receiving an operation command from an infrared remote control. The wireless module may also be a Wi-Fi, a bluetooth, zig-bee or other wireless module for interacting with external devices.

In some embodiments, the wireless module receives a command and sends to the controller. The controller uses the command to change modes or to change controlling behavior depending on the needs of the actual design.

In some embodiments, the light tube apparatus further includes a timer for turning on the sanitizing mode automatically.

In some embodiments, the timer provides the controller a tool to use time factor controlling the first light source and the second light source.

In some embodiments, a clock function may also be embedded to the timer. For example, a battery may be used for keeping the clock function working even when the light tube apparatus is not provided with electricity.

In some embodiments, there is a wall switch electrically connected to the light tube apparatus for controlling the light tube apparatus, the controller sets the timer when receiving a predetermined input pattern.

In some embodiments, the light tube apparatus is installed to a light tube socket disposed on a ceiling. In addition, a wall switch is connected to the light tube apparatus to control the light tube apparatus. The controller may detect the input pattern, e.g. three consecutive clips within 3 seconds, of the wall switch and associate such input pattern with a control function. For example, the wall switch may be used for setting a predetermined input pattern to tell the controller to remember it is time to start sanitizing regularly. If the input pattern is entered in 20:00, the controller remembers by storing the information in a storage device that sanitizing is to be automatically executed 20:00 every day.

In some embodiments, the controller postpones a predetermined time period using the timer for an operator to have time to leave before the sanitizing mode is started.

In some embodiments, the timer may also be used for reserving some time so that people can leave with preparation.

In some embodiments, the light tube apparatus further includes an air moving device for driving an environment air passing by the second light source for sanitizing the environment air.

In some embodiments, an air moving device may be an air suction device, a fan or other device used for driving an environment air to pass by the second light source via an air path.

In some embodiments, the air moving device is operated in the illuminating mode for enhancing heat dissipation of the first light source. The air flow may also be used for enhancing heat dissipation of the light tube apparatus.

In some embodiments, the second window is enclosed so that the ultraviolet light only applies to the environment air, not emitting to users.

In some embodiments, the second window is enclosed, e.g. concealed by the tubular housing of the light tube apparatus. Therefore, the ultraviolet light of the second light source is not emitted outside the light tube apparatus. Instead, there is an air path with air flow driven by an air moving device.

In some embodiments, the first light keeps emitting the white light from the first window in the sanitizing mode.

In some embodiments, when the ultraviolet light is kept inside the light tube apparatus or not directly shown to outside, the first light source may continue providing illumination via the first window. In other words, the illumination mode and the sanitizing mode may be overlapped.

In some embodiments, the controller also informs users the sanitizing mode with a visual effect. For example, there is an indicator like a speaker or a LED indicator showing the status of the light tube apparatus. For example, the indicator may inform users whether the sanitizing mode is turned on.

In some embodiments, the light tube apparatus also includes an environment detector for detecting an environment air quality and shows the environment air quality visually.

In some embodiments, an environment detector may be used for detecting an environment air quality and shows the result via the indicator.

In some embodiments, the light tube apparatus further includes a third light source and an electrode. The third light source attacking mosquitos and the electrode kills the attracted mosquitos. The third light source attracts mosquitos with favorite light frequency of mosquitos and the electrode supplies electrify to kill the attracted mosquitos.

In some embodiments, the controller sends a first command to an external air conditioner for sending air moving to the second light source in the sanitizing mode.

In some embodiments, the controller of the light tube apparatus sends commands to an air conditioner and a fan device together to send air continuously to the light tube apparatus so that the air is passing by the ultraviolet light emitted by the second light source.

Such operation may be activated in the sanitizing mode because under some criteria, there is no one in the detected area. This would be the perfect time for using the air conditioner and the fan device together to make the sanitizing work more completely.

In some embodiments, the controller further sends a second command to a fan together with the air conditioner for sending air moving to the second light source in the sanitizing mode.

In some embodiments, the second light source is disposed on an opposite side of the light source.

In some embodiments, the second light source and the first light source are disposed on opposite sides of a substrate. Therefore, when a user needs to use the sanitizing functions, the user may place the light tube upside down by facing the second light source facing to ground. A pose sensor may be used for determining which side is facing to the ground so that the controller activates one of the first light source and the second light source to turned on to enter either the illuminating mode or the sanitizing mode.

In some embodiments, the controller shows a visual effect to indicate a user a current progress of sanitization.

In some embodiments, the first light source may be used for generating different colors to inform users the progress of the sanitizing process. For example, a red light may inform users that the sanitizing process is on-going. Users see a yellow light for knowing that the sanitizing is almost closed, and the green light to know that the sanitizing process is done.

DETAILED DESCRIPTION

Figure 1:
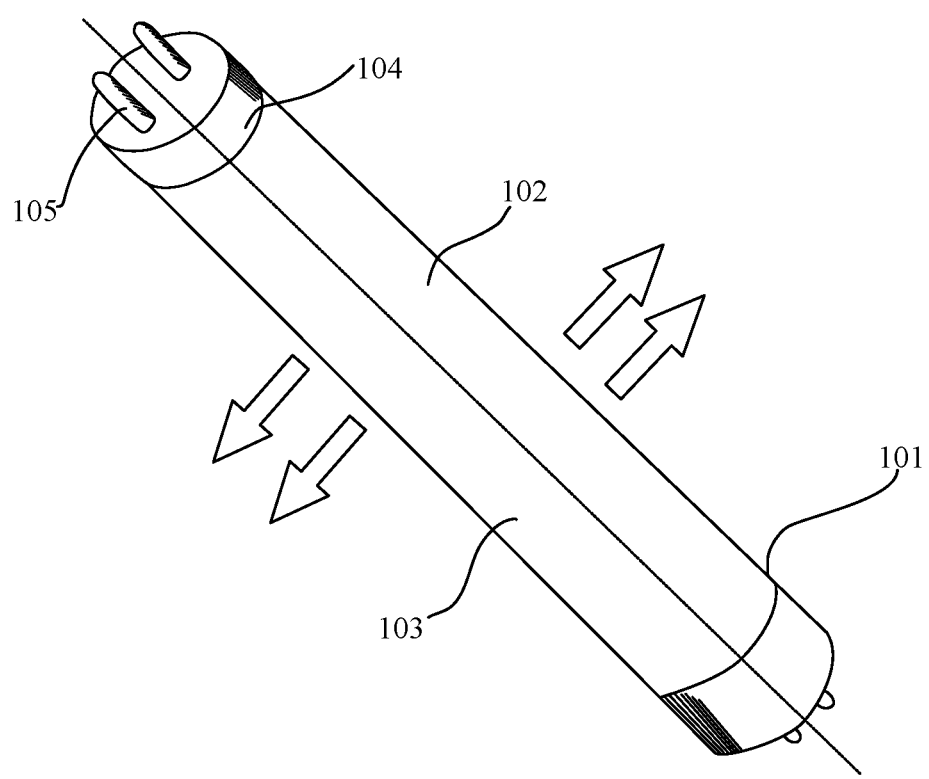
FIG. 1 is a schematic view of a light tube apparatus according to an embodiment of the present disclosure.

Please refer to FIG. 1. In FIG. 1, a light tube apparatus includes a tubular housing 101. There are two end caps 104 fixed on two ends of the tubular housing 101. There are pins 105 fixed the cap end 104 for connecting to a light tube socket to receive electricity from a power source.

In FIG. 1, the light tube apparatus also has a first window 103 and a second window 102 disposed on surface of the tubular housing 101.

Figure 2:
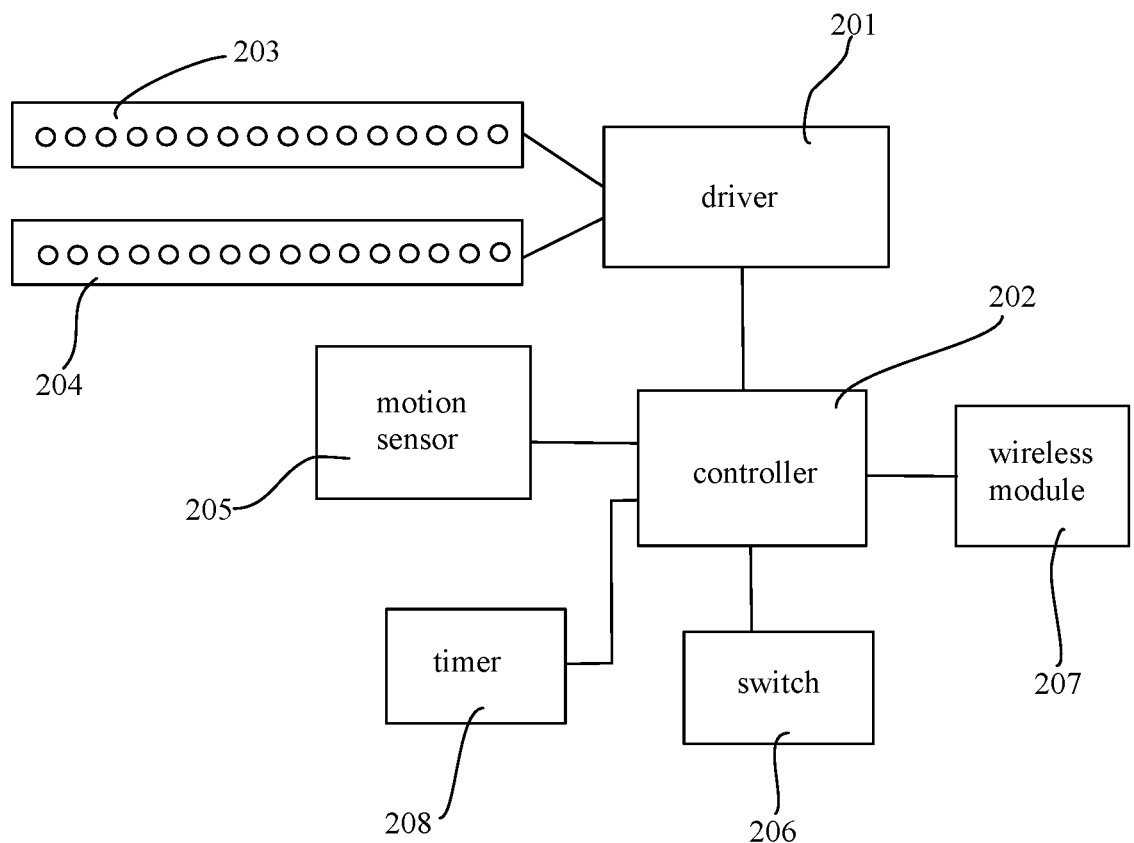
FIG. 2 is a schematic view of a light tube apparatus according to an embodiment of the present disclosure.

Please refer to FIG. 2. In FIG. 2, the light tube apparatus like the one mentioned in FIG. 1 has a first light source 203, a second light source 204, a driver 201 and a controller 202.

The driver 201 converts an external power source like a 110V alternating current power source to a direct current.

The controller 202 contains one or multiple circuits working the driver 201 to control the first light source 203 and the second light source 204. The first light source 203 emits a white light or other light to provide illumination function. The second light source 204 emits an ultraviolet light to provide a sanitizing function. The controller 202 determines when to enter a sanitizing mode in which the second light source 204 is operated to clean air or surface of objects.

In addition to using ultraviolet light for sanitization, the second light source 203 may be used to generate ozone which also has sanitization function.

Usually, people do not want to be exposed to ultraviolet light environment. Therefore, the controller is provided with a criterion to automatically or selectively determine when and whether to enter or pause the sanitizing mode.

There are various ways to arrange the first window and the second window.

Figure 3:
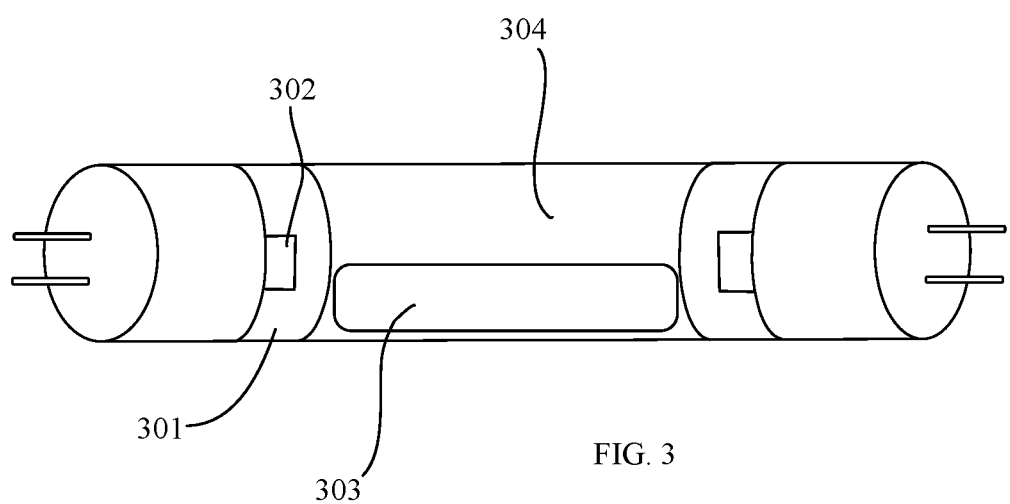
FIG. 3 is a schematic side view of a light tube apparatus according to an embodiment of the present disclosure.

Please refer to FIG. 3. In FIG. 3, the first light source 303 and corresponding first window are located at a central portion of the light tube apparatus. The second light source 302 and the second window 302 are located at two ends of the light tube.

In FIG. 2, there is a motion sensor 205 installed to the light tube apparatus for detecting whether there is person nearby.

For example, the motion sensor 205 may be made of an infrared sensor or a radar sensor. The infrared sensor uses infrared detection of people. The radar sensor uses microwave to detect whether there are people moving near or staying below the light tube.

As mentioned above, the controller uses a criterion, which may be one or multiple rules coded in program or logic circuits in the controller 202, to determine when to enter or to pause the sanitizing mode.

Designers may set the criterion as that when a person nearby is detected by the motion sensor 205, the controller 202 stops the sanitizing mode immediately until the detected person leaves the detected area.

In some embodiments, the criterion may be set that the controller 202 starts the sanitizing mode when no one is detected in the detected area. In other words, when no one is in the place, like a living room or an office, the second light source 204 is turned on to emit ultraviolet light to perform sanitization in the detected area.

The criterion may be more complicated with multiple rules. For example, the controller 202 also refers to a timer 208 to determine whether to enter the sanitizing mode. For example, when the controller 202 finds that it is later than 23:00, the sanitizing mode is turned on until 04:00.

Figure 4A:
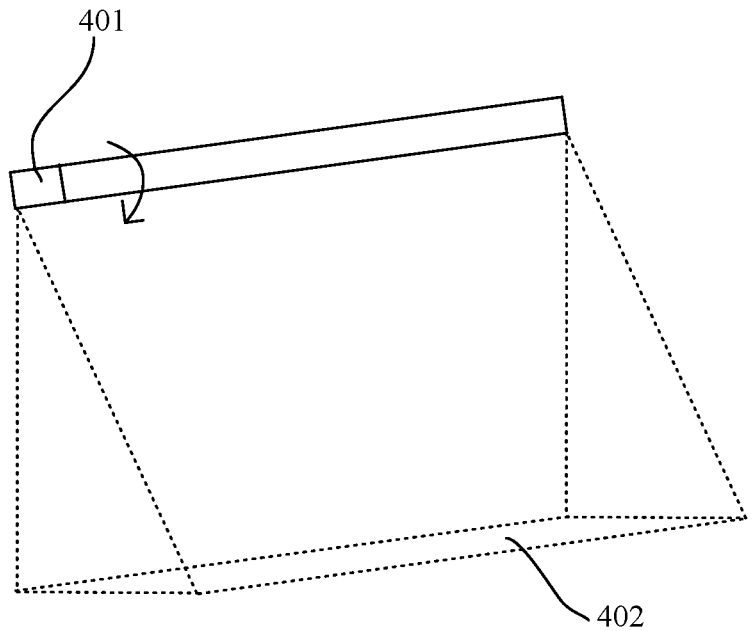
FIG. 4A is a schematic view of a light tube apparatus according to an embodiment of the present disclosure.
Figure 4B:
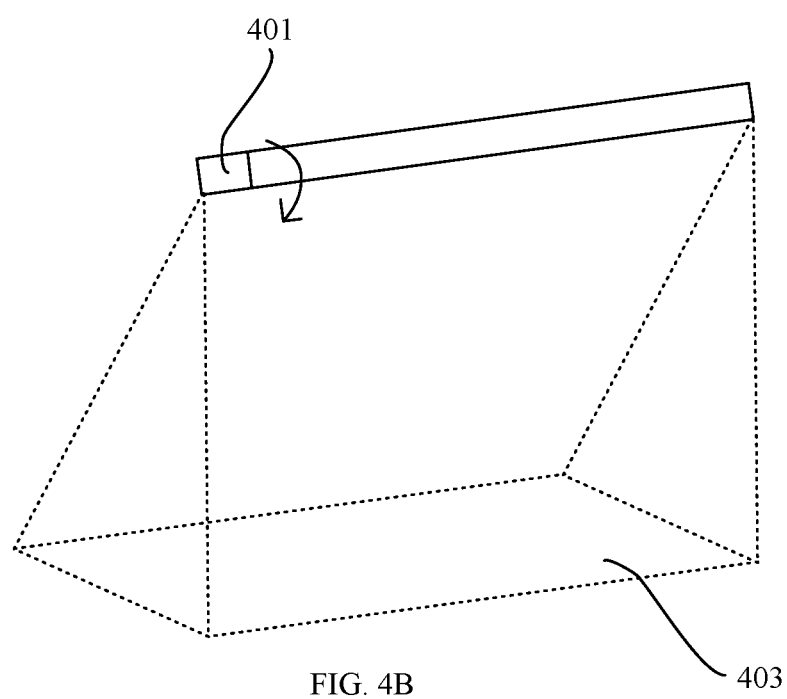
FIG. 4B is a schematic view of a light tube apparatus according to an embodiment of the present disclosure.

Please refer to FIG. 4A and FIG. 4B. In FIG. 4A, the light tube apparatus has a rotation ring 401 for rotating the second window and the second light source, if necessary, to change an emitted zone 402 to 403.

A lens that is used for changing an area size may also be used for adjusting the sanitizing area.

In FIG. 2, the controller 202 may also be connected to a switch 206. The switch 206 may be a manual switch like a jumper disposed on a surface of the light tube apparatus. The switch 206 may also be a voice activated switch or a touch activated switch to turn on, to turn off, to disable or to enable the sanitizing function.

In some embodiments, the switch 206 may be used for changing an operating mode of the light tube. For example, during summer vacation, the light tube may be set by operating the switch 206 to enter the sanitizing mode every day between 23:00 to 05:00 automatically while the first light source module 203 is not turned on.

In FIG. 2, the light tube apparatus may also has a wireless module 207. For example, the wireless module 207 may be an infrared receiver for receiving an operation command from an infrared remote control. The wireless module 207 may also be a Wi-Fi, a bluetooth, zig-bee or other wireless module for interacting with external devices.

The wireless module 207 receives a command and sends to the controller 202. The controller 202 uses the command to change modes or to change controlling behavior depending on the needs of the actual design.

In FIG. 2, the timer 205 provides the controller 202 a tool to use time factor controlling the first light source 203 and the second light source 204.

In some embodiments, a clock function may also be embedded to the timer 208. For example, a battery may be used for keeping the clock function working even when the light tube apparatus is not provided with electricity.

Figure 5:
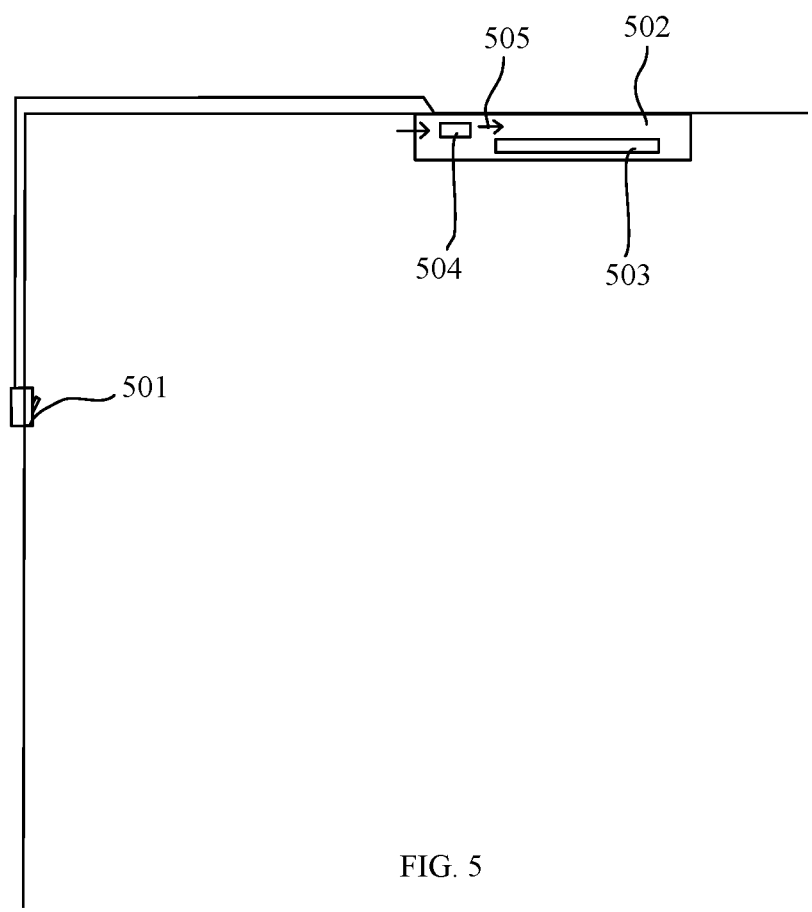
FIG. 5 is a schematic view of a switch and a light tube apparatus according to an embodiment of the present disclosure.

In some embodiments, the light tube apparatus is installed to a light tube socket disposed on a ceiling. In addition, a wall switch, like the example 501 in FIG. 5, is connected to the light tube apparatus to control the light tube apparatus.

The controller may detect the input pattern, e.g. three consecutive clips within 3 seconds, of the wall switch and associate such input pattern with a control function.

For example, the wall switch may be used for setting a predetermined input pattern to tell the controller to remember it is time to start sanitizing regularly. If the input pattern is entered in 20:00, the controller remembers by storing the information in a storage device that sanitizing is to be automatically executed 20:00 every day.

The timer may also be used for reserving some time so that people can leave with preparation.

Please refer to FIG. 5. In FIG. 5, an air moving device 504 like an air suction device, a fan or other device, is used for driving an environment air 505 to pass by the second light source 503 via an air path 502.

The air flow may also be used for enhancing heat dissipation of the light tube apparatus.

Figure 7:
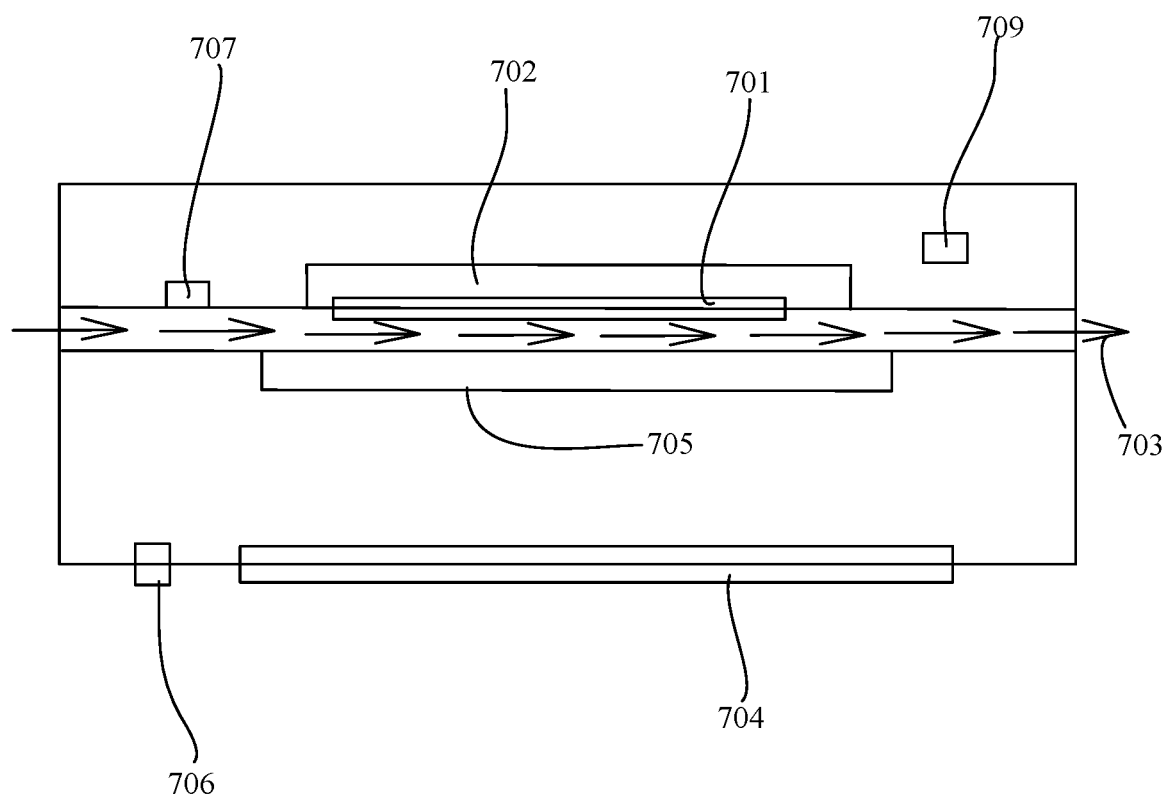
FIG. 7 is a schematic front view of a light tube apparatus according to an embodiment of the present disclosure.

Please refer to FIG. 7. In FIG. 7, the second window 701 is enclosed, e.g. concealed by the tubular housing of the light tube apparatus. Therefore, the ultraviolet light of the second light source 702 is not emitted outside the light tube apparatus. Instead, there is an air path 703 with air flow driven by an air moving device 707.

In FIG. 7, when the ultraviolet light is kept inside the light tube apparatus or not directly shown to outside, the first light source 705 may continue providing illumination via the first window 704. In other words, the illumination mode and the sanitizing mode may be overlapped.

In FIG. 7, there is an indicator 706 like a speaker or a LED indicator showing the status of the light tube apparatus. For example, the indicator 706 may inform users whether the sanitizing mode is turned on.

In FIG. 7, an environment detector 709 may be used for detecting an environment air quality and shows the result via the indicator 706.

Figure 6:
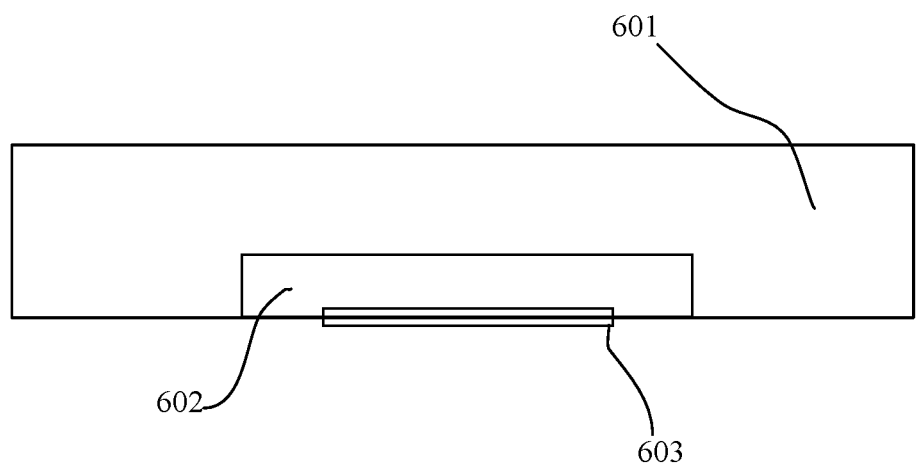
FIG. 6 is a schematic front view of a light tube apparatus according to an embodiment of the present disclosure.

Please refer to FIG. 6. The light tube apparatus 601 further includes a third light source 602 and an electrode 603. The third light source attracts mosquitos with favorite light frequency of mosquitos and the electrode 603 supplies electrify to kill the attracted mosquitos.

Figure 8:
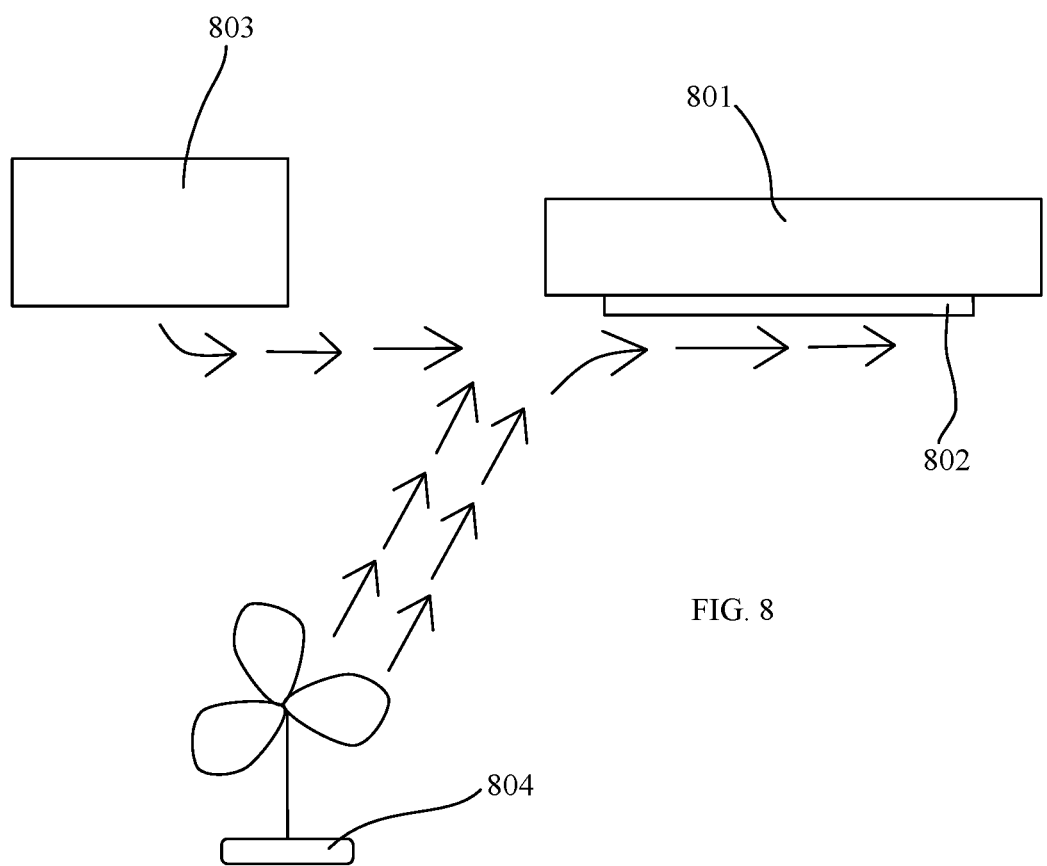
FIG. 8 is a schematic view of a light tube apparatus according to an embodiment of the present disclosure.

Please refer to FIG. 8. In FIG. 8, the controller of the light tube apparatus 801 sends commands to an air conditioner 803 and a fan device 804 together to send air continuously to the light tube apparatus 801 so that the air is passing by the ultraviolet light emitted by the second light source 802.

Such operation may be activated in the sanitizing mode because under some criteria, there is no one in the detected area. This would be the perfect time for using the air conditioner and the fan device together to make the sanitizing work more completely.

Figure 9:
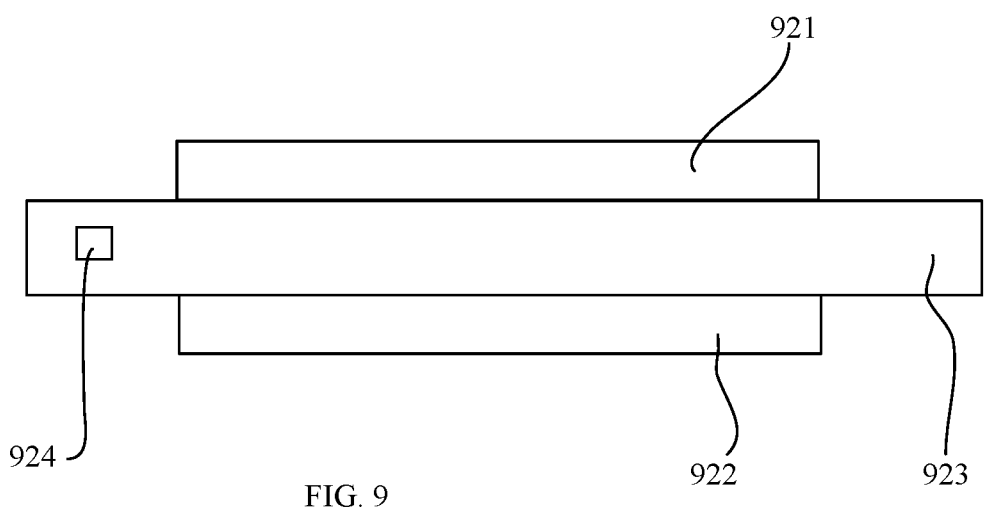
FIG. 9 is a schematic front view of a light tube apparatus according to an embodiment of the present disclosure.

In FIG. 9, the second light source 921 and the first light source 902 are disposed on opposite sides of a substrate 923. Therefore, when a user needs to use the sanitizing functions, the user may place the light tube upside down by facing the second light source 901 facing to ground. A pose sensor 924 may be used for determining which side is facing to the ground so that the controller activates one of the first light source 922 and the second light source 921 to turned on to enter either the illuminating mode or the sanitizing mode.

In some embodiments, the first light source may be used for generating different colors to inform users the progress of the sanitizing process. For example, a red light may inform users that the sanitizing process is on-going. Users see a yellow light for knowing that the sanitizing is almost closed, and the green light to know that the sanitizing process is done.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings.

The embodiments were chosen and described in order to best explain the principles of the techniques and their practical applications. Others skilled in the art are thereby enabled to best utilize the techniques and various embodiments with various modifications as are suited to the particular use contemplated.

Although the disclosure and examples have been fully described with reference to the accompanying drawings, it is to be noted that various changes and modifications will become apparent to those skilled in the art. Such changes and modifications are to be understood as being included within the scope of the disclosure and examples as defined by the claims.

The invention claimed is:

1. A light tube apparatus, comprising: a tubular housing having a first light passing window and a second light passing window; a first light source for emitting a white light from the first light passing window in an illuminating mode; a second light source for emitting an ultraviolet light from the second light passing window in a sanitizing mode; a driver for converting an external power source to a first driving current to the first light source and a second driving current to the second light source; an environment detector for detecting an environment air quality and showing the environment air quality visually; a controller for determining when to enter the sanitizing mode or the illuminating mode based on a stored criterion, wherein the controller informs users of the sanitizing mode with a visual effect, wherein the controller shows a visual effect to indicate to a user a current progress of sanitization; and a timer for turning on the sanitizing mode automatically, wherein there is a wall switch electrically connected to the light tube apparatus for controlling the light tube apparatus, the controller sets the timer when receiving a input pattern applied on the wall switch, wherein a setting time of the timer is associated with the received input pattern, wherein the tubular housing has an infrared receiver electrically connected to the controller for turning on or turning off the sanitizing mode in response to an infrared remote control; and wherein the controller sends a first command to an external air conditioner for sending air moving to the second light source in the sanitizing mode; and further comprising a fan separate from the external air conditioner and tubular housing disposed in the environment in which the tubular housing is installed; wherein the controller further sends a second command to the fan together with the air external conditioner for sending air in the environment moving to the second light source in the sanitizing mode.

2. The light tube apparatus of claim 1, further comprising a motion sensor, wherein the controller pauses the sanitizing mode when a user is detected by the motion sensor.

3. The light tube apparatus of claim 2, wherein the controller automatically determines whether to enter the sanitizing mode when no one is detected by the motion sensor.

4. The light tube apparatus of claim 1, further comprising a rotation ring for rotating the second window so that the ultraviolet light automatically scans a predetermined area.

5. The light tube apparatus of claim 1, wherein the tubular housing has a manual switch electrically connected to the controller for enabling or disabling the sanitizing mode.

6. The light tube apparatus of claim 1, wherein the input pattern comprises a series of consecutive clicks on the wall switch within a predetermined time period.

7. The light tube apparatus of claim 1, wherein the controller postpones a predetermined time period using the timer for an operator to have time to leave before the sanitizing mode is started.

8. The light tube apparatus of claim 1, further comprising a third light source and an electrode, the third light source is configured to attract mosquitos and the electrode is configured to kill the attracted mosquitos.

9. The light tube apparatus of claim 1, wherein the second light source is disposed on an opposite side of the first light source.

10. The light tube apparatus of claim 1, further comprising an air moving device for driving an environment air passing by the second light source for sanitizing the environment air.

11. The light tube apparatus of claim 10, wherein the air moving device is operated in the illuminating mode for enhancing heat dissipation of the first light source.

12. The light tube apparatus of claim 11, wherein the second window is enclosed so that the ultraviolet light only applies to the environment air, not emitting to users.

13. The light tube apparatus of claim 12, wherein the first light keeps emitting the white light from the first window in the sanitizing mode.

* * * * *